United States Patent
Tao et al.

(10) Patent No.: US 11,464,442 B2
(45) Date of Patent: Oct. 11, 2022

(54) METHOD AND APPARATUS FOR DETERMINING QUALITY GRADE OF VIDEO DATA

(71) Applicants: TSINGHUA UNIVERSITY, Beijing (CN); CHINA MOBILE ONLINE SERVICES COMPANY LIMITED, Zhengzhou (CN)

(72) Inventors: Xiaoming Tao, Beijing (CN); Dingcheng Gao, Beijing (CN); Bingrui Geng, Beijing (CN); Yiping Duan, Beijing (CN); Chaoyi Han, Beijing (CN); Qiwei Song, Beijing (CN); Qing Chen, Zhengzhou (CN)

(73) Assignees: TSINGHUA UNIVERSITY, Beijing (CN); CHINA MOBILE ONLINE SERVICES COMPANY LIMITED, Zhengzhou (CN)

( * ) Notice: Subject to any disclaimer, the term of this patent is extended or adjusted under 35 U.S.C. 154(b) by 0 days.

(21) Appl. No.: 17/489,827

(22) Filed: Sep. 30, 2021

(65) Prior Publication Data

US 2022/0095988 A1    Mar. 31, 2022

(30) Foreign Application Priority Data

Sep. 30, 2020    (CN) .......................... 202011068969.4

(51) Int. Cl.
*A61B 5/378* (2021.01)
*A61B 5/384* (2021.01)
(Continued)

(52) U.S. Cl.
CPC .............. *A61B 5/378* (2021.01); *A61B 5/165* (2013.01); *A61B 5/372* (2021.01); *A61B 5/384* (2021.01);
(Continued)

(58) Field of Classification Search
None
See application file for complete search history.

(56) References Cited

FOREIGN PATENT DOCUMENTS

| CN | 109816646 A | * | 5/2019 |
| CN | 109816646 A |   | 5/2019 |

(Continued)

OTHER PUBLICATIONS

Support-vector machine—Wikipedia, Jan. 24, 2019, https://en.wikipedia.org/w/index.php?title=Support-vector_machine&oldid=876691398.

*Primary Examiner* — Michael R Bloch
(74) *Attorney, Agent, or Firm* — Bayramoglu Law Offices LLC

(57) ABSTRACT

The disclosure provides a method and an apparatus for determining a quality grade of video data, and relates to the field of data processing technologies, wherein the method includes: acquiring a plurality of initial EEG data; based on the plurality of initial EEG data, determining an initial EEG data set, wherein the initial EEG data set includes a first sub-data set and a second sub-data set, the first sub-data set is a data set built on the basis of emotional response electroencephalogram data, and the second sub-data set is a data set built on the basis of electroencephalogram emotion data; processing the first sub-data set and the second sub-data set by using a transfer learning algorithm to obtain a third sub-data set and a fourth sub-data set; and based on the third sub-data set and the fourth sub-data set, determining a quality evaluation grade of video data with degraded quality.

9 Claims, 4 Drawing Sheets

(51) Int. Cl.
*A61B 5/372* (2021.01)
*A61B 5/16* (2006.01)
*A61B 5/00* (2006.01)

(52) U.S. Cl.
CPC ............ *A61B 5/726* (2013.01); *A61B 5/7221* (2013.01); *A61B 5/7264* (2013.01)

(56) References Cited

FOREIGN PATENT DOCUMENTS

| | | | | | |
|---|---|---|---|---|---|
| CN | 111510710 | A | * | 8/2020 | ............ G06F 3/015 |
| CN | 111510710 | A | | 8/2020 | |
| EP | 3355766 | B1 | | 8/2019 | |

* cited by examiner

METHOD AND APPARATUS FOR DETERMINING QUALITY GRADE OF VIDEO DATA

CROSS REFERENCE TO THE RELATED APPLICATIONS

This application is based upon and claims priority to Chinese Patent Applications No. 202011068969.4, filed on Sep. 30, 2020, the entire contents of which are incorporated herein by reference.

TECHNICAL FIELD

The present disclosure relates to the field of data processing technologies, and particularly to a method and an apparatus for determining a quality grade of video data.

BACKGROUND

Since a communication bandwidth is difficult to meet a high-quality wideband service, a multimedia service may have various quality degradation phenomena. In a QoE-oriented evaluation method, several common factors for quality degradation of video replaying respectively include: video definition, initial playing buffering, playing lagging, and unsynchronized sound and picture, or the like. Compared with lagging and initial buffering, the unsynchronized sound and picture during playing is more unbearable. After fixed timestamps of the audio and video after coding are transmitted to a receiving end of a user, due to network packet loss, time delay and other network degradation problems, the unsynchronized timestamps will directly lead to various phenomena such as picture resolution, voice disorder, and discontinuous connection.

The score evaluation for this service is usually based on a subjective score of the user directly. In an experimental environment, a stimulus material with unsynchronized sound and picture is played for a target object, and the target object judges whether the experimental material has the phenomenon of unsynchronized sound and picture according to a subjective feeling, and then gives a corresponding score for a degree of feeling of the unsynchronized sound and picture according to a score table. Common score tables include an MOS score table, a double stimulus continuous quality score scale, and the like. Results of all target objects are comprehensively counted, and a mean score is acquired as a result of the subjective scoring of the user.

However, unsynchronized sound and picture quality scoring methods directly based on the subjective scoring of the user, such as a double stimulus impairment scale, a double stimulus continuous quality scale, single stimulus, and the like, are directly used to subjectively score the material with unsynchronized sound and picture. Each sequence and each unsynchronized sound and picture grade class are averagely scored by the double stimulus impairment scale, while two random sequences are scored by the double stimulus continuous quality scale, and a difference of the scores is used as a final evaluation index. These methods are all influenced by personal subjectivity and prejudice of the target object in the test, and are often mixed with personal experience. The results are too isolated, which are not beneficial for generalization of the results, and a standard experience quality evaluation system cannot be formed.

Aiming at the above problems, no effective solution has been proposed yet.

SUMMARY

Considering this, the present disclosure aims at providing a method and an apparatus for determining a quality grade of video data, to solve a technical problem of relatively low accuracy of an obtained evaluation result when an emotion classification model is used for determining the quality grade of the video in the prior art.

According to a first aspect, the embodiments of the present disclosure provide a method for determining a quality grade of video data, including: acquiring a plurality of initial electroencephalogram (EEG) data, wherein the initial EEG data includes: electroencephalogram emotion data generated by a target object watching video data with degraded quality, and emotional response electroencephalogram data generated by the target object watching an emotional picture or an emotional video; based on the plurality of initial EEG data, determining an initial EEG data set, wherein the initial EEG data set includes a first sub-data set and a second sub-data set, the first sub-data set is a data set built on the basis of the emotional response electroencephalogram data, and the second sub-data set is a data set built on the basis of the electroencephalogram emotion data; processing the first sub-data set and the second sub-data set by using a transfer learning algorithm to obtain a third sub-data set and a fourth sub-data set; and based on the third sub-data set and the fourth sub-data set, determining a quality evaluation grade of the video data with degraded quality.

Further, the method includes: preprocessing the plurality of initial EEG data to obtain a plurality of target EEG data; performing characteristic extraction on the plurality of target EEG data to obtain a plurality of wavelet packet coefficient characteristics; building the first sub-data set by using the wavelet packet coefficient characteristic of the electroencephalogram emotion data, and building the second sub-data set by using the wavelet packet coefficient characteristic of the emotional response electroencephalogram data; and determining a collection of the first sub-data set and the second sub-data set as the initial EEG data set.

Further, the step of preprocessing the plurality of initial EEG data to obtain the plurality of target EEG data includes: determining a reference potential of the initial EEG data; based on the reference potential, calibrating the initial EEG data to obtain intermediate EEG data; and filtering and clipping the intermediate EEG data to obtain the target EEG data.

Further, the initial EEG data includes a plurality of scalp electrode signals; and the step of determining the reference potential of the initial EEG data includes: determining location information of an electrode corresponding to each scalp electrode signal on a scalp of the target object; using the location information to determine a target location, and according to a potential of an electrode corresponding to the target location, determining the reference potential, wherein the target location refers to bilateral ears of the target object; or calculating a mean potential of potentials corresponding to the plurality of scalp electrode signals; and determining the mean potential as the reference potential.

Further, the step of filtering and clipping the intermediate EEG data to obtain the target EEG data includes: filtering the intermediate EEG data to obtain the filtered intermediate EEG data; performing independent principal components analysis on the filtered intermediate EEG data to determine a target signal in the filtered intermediate EEG data, wherein the target signal is a signal with a maximum energy value in the filtered intermediate EEG data; and deleting the target signal to obtain the target EEG data.

Further, the step of performing characteristic extraction on the plurality of target EEG data to obtain the plurality of wavelet packet coefficient characteristics includes: performing wavelet packet decomposition on the target EEG data to obtain a sub-band tree, wherein each sub-band contains one or more nodes; determining a wavelet packet coefficient of each sub-band; and based on the wavelet packet coefficient of each sub-band, extracting the wavelet packet coefficient characteristic, wherein the wavelet packet coefficient characteristic includes: wavelet energy of each node, the wavelet entropy of each node, the energy recursion efficiency of the target waveband, and the absolute power.

Further, the step of, based on the third sub-data set and the fourth sub-data set, determining the quality evaluation grade of the video data with degraded quality includes: based on the third sub-data set, building a support vector machine model; and inputting the fourth sub-data set into the support vector machine model to obtain the quality evaluation grade of the video data with degraded quality.

According to a second aspect, the embodiments of the present disclosure further provide an apparatus for determining a quality grade of video data, including: an acquisition unit, a first building unit, a second building unit and an execution unit, wherein the acquisition unit is configured for acquiring a plurality of initial EEG data, and the initial EEG data includes: electroencephalogram emotion data generated by a target object watching video data with degraded quality, and emotional response electroencephalogram data generated by the target object watching an emotional picture or an emotional video; the first building unit is configured for, based on the plurality of initial EEG data, determining an initial EEG data set, wherein the initial EEG data set includes a first sub-data set and a second sub-data set, the first sub-data set is a data set built on the basis of the emotional response electroencephalogram data, and the second sub-data set is a data set built on the basis of the electroencephalogram emotion data; the second building unit is configured for processing the first sub-data set and the second sub-data set by using a transfer learning algorithm to obtain a third sub-data set and a fourth sub-data set; and the execution unit is configured for, based on the third sub-data set and the fourth sub-data set, determining a quality evaluation grade of the video data with degraded quality.

Further, the first building unit is configured for: preprocessing the plurality of initial EEG data to obtain a plurality of target EEG data; performing characteristic extraction on the plurality of target EEG data to obtain a plurality of wavelet packet coefficient characteristics; and based on the plurality of wavelet packet coefficient characteristics, building the initial EEG data set.

According to a third aspect, the embodiments of the present disclosure provide an electronic device, including a memory and a processor, wherein the memory is configured for storing a program supporting the processor to execute the method according to the first aspect, and the processor is configured for executing the program stored in the memory.

According to a fourth aspect, the embodiments of the present disclosure provide a computer-readable storage medium, wherein a computer program is stored in the computer-readable storage medium, and the computer program, when executed by a processor, implements the steps of the method according to the first aspect.

In the embodiments of the present disclosure, the plurality of initial EEG data are acquired, wherein the initial EEG data includes: the electroencephalogram emotion data generated by the target object watching the video data with degraded quality, and the emotional response electroencephalogram data generated by the target object watching the emotional picture or the emotional video; based on the plurality of initial EEG data, determining the initial EEG data set, wherein the initial EEG data set includes the first sub-data set and the second sub-data set, the first sub-data set is the data set built on the basis of the emotional response electroencephalogram data, and the second sub-data set is the data set built on the basis of the electroencephalogram emotion data; processing the first sub-data set and the second sub-data set by using the transfer learning algorithm to obtain the third sub-data set and the fourth sub-data set; and based on the third sub-data set and the fourth sub-data set, determining the quality evaluation grade of the video data with degraded quality.

In the embodiments of the present disclosure, the electroencephalogram emotion data is introduced into the existing subjective quality evaluation method, which gets rid of impersonality caused by personal prejudice and historical background in the subjective scoring of the target object, and grades the video data with degraded quality and the subjective quality scores by using transfer learning. Compared with the method of directly using the emotion classification model to evaluate the quality of the video with degraded quality before transfer, the accuracy of the method for determining the quality grade of the video data combined with the transfer learning method has been improved to a certain extent, thus achieving the purpose of improving the evaluation accuracy of the video data with degraded quality, and further solving the technical problem of relatively low accuracy of the obtained evaluation result when the emotion classification model is used for evaluating the quality grade of the video in the prior art, thus achieving the technical effect of improving the evaluation accuracy of the video data with degraded quality.

Other characteristics and advantages of the present disclosure will be elaborated in the following description, and will be partially obvious from the description, or may be learned by practice of the present disclosure. The objects and other advantages of the present disclosure may be realized and attained by the structure particularly pointed out in the specification, claims, and the drawings.

To make the above objects, characteristics and advantages of the present disclosure more obvious and easier to understand, the preferred embodiments will be described in detail below in conjunction with the attached drawings.

BRIEF DESCRIPTION OF THE DRAWINGS

To illustrate the technical solutions in the embodiments of the present disclosure or in the related art more clearly, the drawings used in the description of the embodiments or the prior art will be briefly described below. Obviously, the drawings in the following description are merely some embodiments of the present disclosure. For those of ordinary skills in the art, other drawings can also be obtained based on these drawings without going through any creative work.

DETAILED DESCRIPTION OF THE EMBODIMENTS

To make the objects, technical solutions and advantages of the embodiments of the present disclosure clearer, the following clearly and completely describes the technical solutions of the present disclosure with reference to the drawings. Apparently, the described embodiments are merely some but not all of the embodiments of the present disclosure. Based on the embodiments of the present disclosure, all other embodiments obtained by those of ordinary skills in the art without going through any creative work shall fall within the protection scope of the present disclosure.

First Embodiment

According to the embodiments of the present disclosure, an embodiment of a method for determining a quality grade of video data is provided. It should be noted that the steps shown in the flow chart of the drawings may be executed in a computer system such as a set of computer-executable instructions, and, although a logical sequence is shown in the flow chart, in some cases, the steps shown or described may be executed in a sequence different from that herein.

Figure 1:
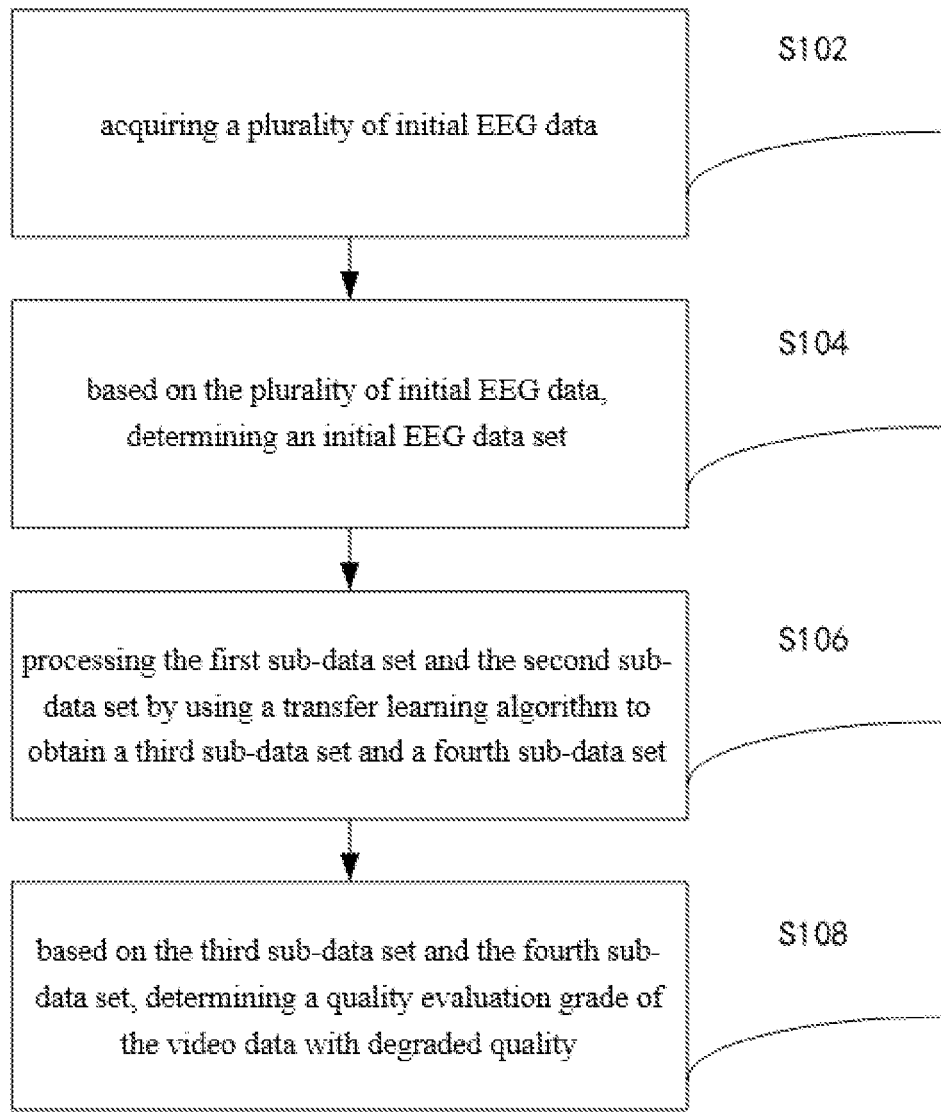
FIG. 1 is a flow chart of a method for determining a quality grade of video data provided by an embodiment of the present disclosure.

FIG. 1 is a flow chart of a method for determining a quality grade of video data according to an embodiment of the present disclosure. As shown in FIG. 1, the method includes the following steps of:

Step S102: acquiring a plurality of initial EEG data, wherein the initial EEG data includes: electroencephalogram emotion data generated by a target object watching video data with degraded quality, and emotional response electroencephalogram data generated by the target object watching an emotional picture or an emotional video;

it should be noted that the EEG (Electroencephalogram) data is electroencephalogram data.

Step S104: based on the plurality of initial EEG data, determining an initial EEG data set, wherein the initial EEG data set includes a first sub-data set and a second sub-data set, the first sub-data set is electroencephalogram emotion data generated on the basis of watching a video data with degraded quality, and the second sub-data set is emotional response electroencephalogram data generated on the basis of watching an emotional picture or an emotional video;

Step S106: processing the first sub-data set and the second sub-data set by using a transfer learning algorithm to obtain a third sub-data set and a fourth sub-data set; and Step S108: based on the third sub-data set and the fourth sub-data set, determining a quality evaluation grade of the video data with degraded quality.

In the embodiments of the present disclosure, the electroencephalogram emotion data is introduced into the existing subjective quality evaluation method, which gets rid of impersonality caused by personal prejudice and historical background in the subjective scoring of the target object, and grades the video data with degraded quality and the subjective quality scores by using transfer learning. Compared with the method of directly using the emotion classification model to evaluate the quality of the video with degraded quality before transfer, the accuracy of the method for determining the quality grade of the video data combined with the transfer learning method has been improved to a certain extent, thus achieving the purpose of improving the evaluation accuracy of the video data with degraded quality, and further solving the technical problem of relatively low accuracy of the obtained evaluation result when the emotion classification model is used for evaluating the quality grade of the video in the prior art, thus achieving the technical effect of improving the evaluation accuracy of the video data with degraded quality.

It should be noted that the above electroencephalogram emotion data may be acquired through experiments, and the specific acquisition method is as follows:

There are two different cases in the unsynchronized audio and video phenomenon of the video data in which the sound is in front of the picture and the picture is in front of the sound, so the grades set in the experiment include 20 grades in total, including 700 ms, 600 ms, 500 ms, 400 ms, 300 ms, 250 ms, 200 ms, 150 ms, 100 ms, 50 ms, 0 ms, −50 ms, −100 ms, −150 ms, −200 ms, −250 ms, −300 ms, −350 ms, −400 ms and −500 ms, with positive numbers indicating that the picture is in front of the sound, while negative numbers indicating that the picture is behind the sound. These two cases are used as experimental groups, while the 0 ms grade group without sound and picture delay is used as a control group for control experiment.

The unsynchronized sound and picture stimulate the material, which intercepts a broadcast content of event comments for 20 seconds, in which an announcer speaks at a moderate speed, enunciates clearly, the video has no exciting content, and the content of the video will not cause any emotion of the target object. The stimulated material consists of three broadcast short films with different contents, which are played at a resolution of 720*576 and a speed of 30 fps.

A pre-experiment will be carried out before starting the experiment, and test preparation will include vision test and pre-experiment. The vision test is to ensure the normal and clear viewing of the target object. In the pre-experiment, the target object will be told our experimental purpose and tasks that the subject needs to complete in the experiment. The target object is guided to use a testing device, and the target object is guided to relax in an unfamiliar shielded room. When the target object is familiar with all the experimental processes, the formal experiment will begin. When the target object presses an Enter key in the shielded room, the experiment will begin formally. An experimenter recorded the electroencephalogram data of the target object during the experiment outside the shielded room, and observes a mental status of the target object during the whole experiment by a monitor. If there is any problem, the experiment is suspended immediately.

There are 120 segments of video data, each of which is an experiment stimulus material with a duration about 20 s. The video data is divided into three chapters to play according to the video content. There will be a black screen between every two chapters, so that the target object can rest for 5 minutes. To prevent the target object from discovering rules between the videos, all 40 videos played between each chapter are disrupted, and randomly selected and played out of order. A size of the screen video in the experiment is 16.8 cm×16.8 cm. A viewing distance is ensured to be around 90 cm.

After each video is played, there will be a problem. The problem is to simply ask whether the target object feels the phenomenon of unsynchronized sound and picture, and the target object only needs to answer yes or no. The question answering link is mainly to ensure an experimental status of the target object, and meanwhile, the result may be finally used as behavioral data of the target object for analysis, and as an auxiliary means for the validity of the electroencephalogram emotion data of the target object. After the problem is over, next video is played. To ensure that the mood of the target object is restored to calm, next prompt will be given before the video is played.

In the experiment, a sampling rate of the initial EEG data of the target object collected by the 64-channel EEG amplifier is 500 Hz, and the 64 electrodes placed on the EEG cap are respectively: FP1-2; AFz, 3-4, 7-8; Fz1-8; FC1-6; FT7-10; Cz,1-6; T7-8; CPz,1-6; TP7-10; Pz,1-8; POz3-4,7-8; Oz,1-2; and Lz. These 64 electrode points also meet the international standard 10-20. In each experiment, the model of the used electroencephalogram cap needs to be judged according to a head shape of the target object, and then the electroencephalogram cap is adjusted to an appropriate location according to an occipital bone and an eyebrow center location of the target object as well as left and right earlobes. The two electrodes TP9 and TP10 are used as the reference of the whole mean potential, and the grounded electrode GND is between Fp1 and Fp2. Before the experiment, all the electrodes need to be coated with conductive paste to ensure that an impedance is below 10 KΩ.

In the embodiments of the present disclosure, the step S104 includes the following steps of:

Step S11: preprocessing the plurality of initial EEG data to obtain a plurality of target EEG data;

Step S12: performing characteristic extraction on the plurality of target EEG data to obtain a plurality of wavelet packet coefficient characteristics; and Step S13: building the first sub-data set by using the wavelet packet coefficient characteristic of the electroencephalogram emotion data, and building the second sub-data set by using the wavelet packet coefficient characteristic of the emotional response electroencephalogram data.

It should be noted that initial EEG data may be preprocessed in environments of Matlab and EEGlab, wherein the preprocessing includes: scalp electrode positioning, reference electrode reselection, filtering, independent principal components analysis and data clipping.

In the embodiments of the present disclosure, the initial EEG data includes a plurality of scalp electrode signals. The plurality of scalp electrode signals mentioned above are collected by electroencephalogram caps arranged on a head of the target object. Generally, 32, 64 or 128 electroencephalogram caps of various models are arranged on the head of the target object, and the electroencephalogram caps are placed according to an international 10-20 system.

Preferably, in this application, 64 electroencephalogram caps of various models are arranged on the head of the target object.

Therefore, the step S11 further includes the following steps of:

Step S111: determining location information of an electrode corresponding to each scalp electrode signal on a scalp of the target object;

Step S112: using the location information to determine a target location, and according to a potential of an electrode corresponding to the target location, determining the reference potential, wherein the target location refers to bilateral ears of the target object; or Step S113: calculating a mean potential of potentials corresponding to the plurality of scalp electrode signals; and Step S114: determining the mean potential as the reference potential.

Specifically, after the initial EEG data is imported to an EEGlab, the EEGlab only displays names and values of the scalp electrode signals collected by each electroencephalogram cap, but the EEGlab cannot s determine a location of each electroencephalogram cap on the scalp of the target object. Therefore, it is necessary to load location information matching the scalp electrode signals to ensure that locations of the plurality of scalp electrode locations will not deviate, so as to ensure that each scalp electrode signal is reasonable and effective.

As the collected scalp electrode signals are individual values, that is, a potential difference between the corresponding location of the electrode of each scalp electrode signal electrode and the reference electrode, in general, a GND electrode is automatically selected as a reference potential point of all the electrodes.

To improve a data accuracy of the initial EEG data, the mean potential of the scalp electrode signals corresponding to bilateral ears of the target object or the mean potential of the potentials corresponding to the plurality of scalp electrode signals may be used as the reference potential.

After the reference potential is determined, the initial EEG data is calibrated to obtain intermediate EEG data.

After the intermediate EEG data is obtained, the intermediate EEG data needs to be filtered and clipped to obtain the target EEG data.

Specifically, the step S13 includes the following steps of:

Step S131: filtering the intermediate EEG data to obtain the filtered intermediate EEG data;

Step S132: performing independent principal components analysis on the filtered intermediate EEG data to determine a target signal in the filtered intermediate EEG data, wherein the target signal is a signal with a maximum energy value in the filtered intermediate EEG data; and Step S133: deleting the target signal to obtain the target EEG data.

In the embodiments of the present disclosure, since the initial EEG data is affected by various electromagnetic noises and power frequency noises in the acquisition process, it is necessary to select and use various filters to filter out the influence of these noises on the electroencephalogram emotion data.

Since the Principal Components Analysis (PCA) is only valid for sample points with Gaussian distribution, while ICA is valid for other distributions except Gaussian distribution, ICA is generally used for electroencephalogram emotion data analysis. Meanwhile, because a number of hidden factors and a number of characteristics are equal in the ICA analysis, independent characteristic signals with the same number as the scalp electrode signals will be obtained from the intermediate EEG data after ICA conversion. Among these characteristic signals, an eye movement signal is the biggest noise, which can be deleted according to the results.

There will be no blinking data in the electroencephalogram emotion data obtained after deleting the eye movement signal in the intermediate EEG data, but since the deleted data may delete many useful data together, the signal with the maximum energy value (i.e., the target signal) is generally deleted.

It should be noted that after obtaining the target EEG data, the target EEG data may be clipped again, and unnecessary channel information and certain time period information in the target EEG data may be removed at this time, which are unnecessary to be included in subsequent analysis, thus reducing a complexity of the subsequent analysis.

In the embodiments of the present disclosure, the step S106 further includes the following steps of:

Step S21: performing wavelet packet decomposition on the target EEG data to obtain a sub-band tree, wherein each sub-band contains one or more nodes;

Step S22: determining a wavelet packet coefficient of each sub-band; and

Step S23: based on the wavelet packet coefficient of each sub-band, extracting the wavelet packet coefficient characteristic, wherein the wavelet packet coefficient characteristic includes: wavelet energy of each node, the wavelet entropy of each node, the energy recursion efficiency of the target waveband, and the absolute power.

Figure 2:
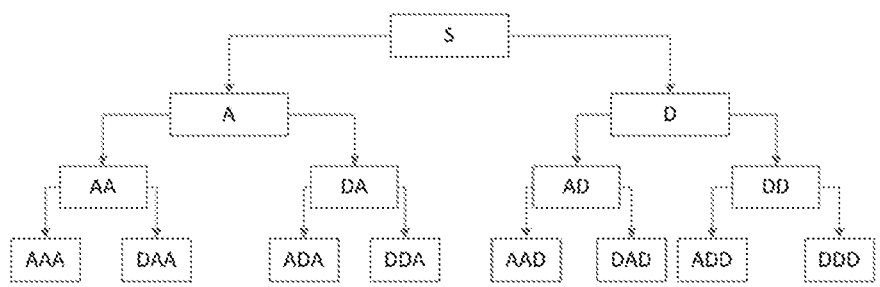
FIG. 2 is a schematic diagram of wavelet packet decomposition provided by the embodiment of the present disclosure.

In the embodiments of the present disclosure, firstly, wavelet packet decomposition is performed on the target EEG data by using the schematic diagram of wavelet packet decomposition as shown in FIG. 2 to obtain the subband tree.

Then, the wavelet packet coefficient of each sub-band is determined, and the wavelet packet coefficient characteristic is extracted according to the wavelet packet coefficient of each sub-band, wherein the wavelet packet coefficient characteristic includes: wavelet energy of each node, the wavelet entropy of each node, the energy recursion efficiency of the target waveband, and the absolute power.

Specifically, a calculation formula of the wavelet energy of each node is as follows:

$$E_{j,i} = \Sigma_{k \in Z}[p_s(n,j,k)]^2$$

$$E_j = \Sigma_{i=2^n} E(j,i)$$

wherein, $E_{j,i}$ represents an energy value of an $i^{th}$ node on a decomposed sub-band j; $p_s(n,j,k)$ is a wavelet packet transform coefficient, and $E_j$ represents total energy of the wavelet coefficient in this layer. Generally, the energy of each node is calculated and normalized, that is, a percentage of the energy of each node in the total energy is calculated.

a calculation formula of the wavelet entropy of each node is as follows:

Firstly, it is assumed that a probability that the signal energy contained in the $i^{th}$ node exists in this scale is:

$$p_{j,i} = \frac{E_{j,i}}{E_j}$$

$$S_i = -\sum_j p_{j,i} \log p_{j,i}$$

wherein, a wavelet entropy of the $i^{th}$ node is $S_i$.

Target wavebands include γ, δ, θ, α, β, and the like. An energy recursive efficiency calculation formula of the target wavebands is as follows:

$$REE_{gamma} = \frac{E_{gamma}}{E_{total}}$$

wherein, $E_{gamma}$ represents an energy value on the waveband γ, and $E_{total}$ represents the total energy of the wavelet packet coefficient of the sub-band.

a calculation formula of the absolute power is as follows:

$$P_x = \lim_{T \to \infty} \frac{1}{T} \int_0^T |x(t)|^2 dt$$

After the plurality of wavelet packet coefficient characteristics corresponding to the plurality of target EEG data are extracted, the initial EEG data set is built by using the plurality of wavelet packet coefficient characteristics.

Next, the first sub-data set and the second sub-data set are processed by using a transfer learning algorithm to obtain a third sub-data set and a fourth sub-data set.

Specifically, according to characteristic-based transfer learning, there is one characteristic mapping Ø by assuming in Transfer Component Analysis (TCA), so that data distributions P(Ø($X_s$)) and P(Ø($X_t$)) of originally unequal P($X_s$) and P($X_t$) are approximately equal after mapping. If edge distributions are close, then the conditional distributions will also be closed. In other words, the conditional distribution of the final result P($y_s$|Ø($X_s$)) is approximately equal to P($y_t$|Ø($X_t$)).

To find this suitable Ø is to solve the question of minimize a distance between a source domain and a target domain, for the distance problem, Euclidean distance, cosine similarity, Mahalanobis distance and so on are commonly used. Maximum Mean Discrepancy (MMD) is used in TCA. If m and n represent number of samples in the source domain and the target domain respectively, MMD may be expressed as:

$$d(X_s, X_t)^2 = MMD^2 = \left\| \frac{1}{m}\sum_{i=1}^{m}\phi(X_i) - \frac{1}{n}\sum_{j=1}^{n}\phi(X_j) \right\|^2.$$

In the embodiments of the present disclosure, the step S108 includes the following steps of:

Step S31: based on the third sub-data set, building a support vector machine model; and Step S32: inputting the fourth sub-data set into the support vector machine model to obtain the quality evaluation grade of the video data with degraded quality.

In the embodiments of the present disclosure, after obtaining the third sub-data set and the fourth sub-data set, the support vector machine model is built by using the third sub-data set, and then the fourth sub-data set is input into the support vector machine model, so that the support vector machine model can determine the quality evaluation grade of the video data with degraded quality according to the fourth sub-data set.

The method above is further explained with reference to the specific example hereinafter.

To verify an experimental effect of the present disclosure, a public data set eNTERFACE 2006 Project #7 is used as the electroencephalogram emotion data, data of the eNTERFACE 2006 Project #7 is used as the data set in the source domain processed in this time, while the data set in the target domain uses the electroencephalogram data with unsynchronized sound and picture acquired by itself. The EEG signals used in the two data sets are acquired by a 64-channel EEG amplifier. Since the minimum frequency of the data set in the source domain is only 256 Hz, all the data sets are uniformly down-sampled to 256 Hz. 64 electrodes placed on EEG caps are: Fpz,1-2; AFz,3-4,7-8; Fz1-8; FCz,1-6; FT7-8; Cz,1-6; T7-8; CPz,1-6; TP7-8; Pz,1-10; POz3-4,7-8; Oz,1-2; and Lz. These 64 electrode points also meet the international standard 10-20. By comparing channels of the two data sets, 52 electrodes are finally used, and the 12 electrodes including Fpz,1-2, AFz,7,8, F5-8, Cz and FCz are excluded. However, because channel sequences of the two data sets are inconsistent, it is necessary to reorder the channel sequences after characteristic extraction.

The two data are first read by Matlab and EEGlab, and subjected to scalp positioning. Then potential averaging is performed. Because there are no TP9 and TP10 electrodes in the data set of the source domain, global potential averaging is still used. For filtering, the same band-pass filter of 4 Hz to 45 Hz is used to filter out power frequency noises in the signal, and finally electromyographic signals and eye movement signals are removed. ICA is also used for principal components analysis, and clutter data is removed according to Adjust and individual experience.

After the preprocessing is finished, the data is clipped, and the data sets in the target domain and the source domain are clipped with the same operation. A total of 3*19*5=285 segments are cut out for each subject in the target domain, and the cut segments are subjected to wavelet packet decomposition as in the previous chapter. The characteristics such as the energy, the wavelet entropy and the absolute power are calculated respectively, and the same characteristics as those in the source domain are obtained.

However, an accuracy of re-classifying the unsynchronized sound and picture in the model is obviously increased, wherein the accuracy of all classifiers has exceeded 40%, and the accuracy of random forest and polynomial-based SVM model has obviously increased, both exceeding 50%, and the mean accuracy of the latter has reached about 54%, which is a significant increase compared with the SVM without transfer.

Second Embodiment

The embodiments of the present disclosure also provide an apparatus for determining a quality grade of video data. The apparatus for determining the quality grade of the video data is configured for executing the method for determining a quality grade of video data provided by the above-mentioned embodiment of the present disclosure. The following is a detailed introduction of the apparatus for determining the quality grade of the video data provided by the embodiments of the present disclosure.

Figure 3:
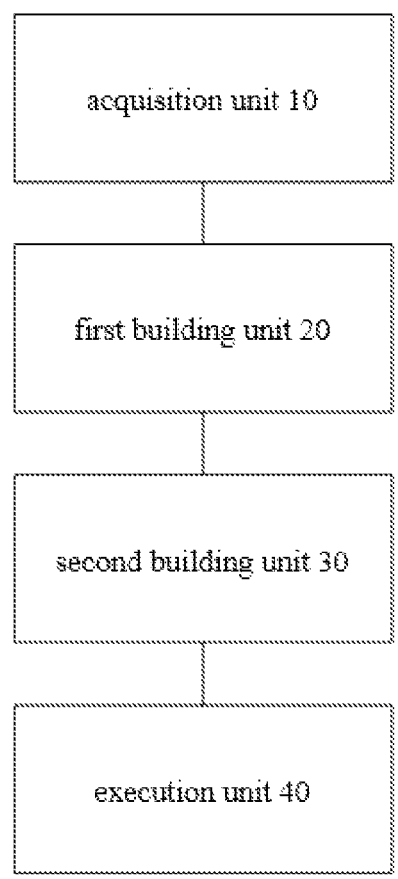
FIG. 3 is a schematic diagram of an apparatus for determining a quality grade of video data provided by an embodiment of the present disclosure.

As shown in FIG. 3, FIG. 3 is a schematic diagram of the apparatus for determining the quality grade of the video data mentioned above. The apparatus for determining the quality grade of the video data includes: an acquisition unit 10, a first building unit 20, a second building unit 30 and an execution unit 40.

The acquisition unit 10 is configured for acquiring a plurality of initial EEG data, wherein the initial EEG data includes: electroencephalogram emotion data generated by a target object watching video data with degraded quality, and emotional response electroencephalogram data generated by the target object watching an emotional picture or an emotional video;

the first building unit 20 is configured for, based on the plurality of initial EEG data, determining an initial EEG data set, wherein the initial EEG data set includes a first sub-data set and a second sub-data set, the first sub-data set is a data set built on the basis of the emotional response electroencephalogram data, and the second sub-data set is a data set built on the basis of the electroencephalogram emotion data;

the second building unit 30 is configured for processing the first sub-data set and the second sub-data set by using a transfer learning algorithm to obtain a third sub-data set and a fourth sub-data set; and the execution unit 40 is configured for, based on the third sub-data set and the fourth sub-data set, determining a quality evaluation grade of the video data with degraded quality.

In the embodiments of the present disclosure, the electroencephalogram emotion data is introduced into the existing subjective quality evaluation method, which gets rid of impersonality caused by personal prejudice and historical background in the subjective scoring of the target object, and grades the video data with degraded quality and the subjective quality scores by using transfer learning. Compared with the method of directly using the emotion classification model to evaluate the quality of the video with degraded quality before transfer, the accuracy of the method for determining the quality grade of the video data combined with the transfer learning method has been improved to a certain extent, thus achieving the purpose of improving the evaluation accuracy of the video data with degraded quality, and further solving the technical problem of relatively low accuracy of the obtained evaluation result when the emotion classification model is used for evaluating the quality grade of the video in the prior art, thus achieving the technical effect of improving the evaluation accuracy of the video data with degraded quality.

Third Embodiment

The embodiments of the present disclosure also provide an electronic device, including a memory and a processor, wherein the memory is configured for storing a program supporting the processor to execute the method according to the first embodiment, and the processor is configured for executing the program stored in the memory.

Figure 4:
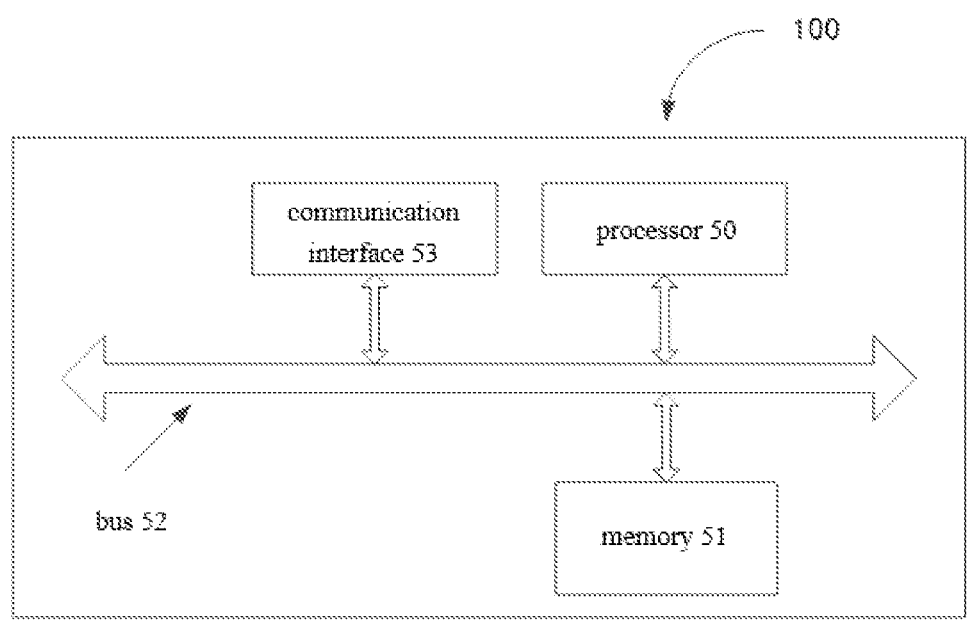
FIG. 4 is a schematic diagram of an electronic device provided by an embodiment of the present disclosure.

Referring to FIG. 4, the embodiments of the present disclosure also provide an electronic device 100, including: a processor 50, a memory 51, a bus 52 and a communication interface 53. The processor 50, the communication interface 53 and the memory 51 are connected through the bus 52. The processor 50 is configured to execute executable modules, such as computer programs, stored in the memory 51.

The memory 51 may probably include a high speed Random Access Memory (RAM), and may also probably include a non-volatile memory, for example, at least one disk memory. Communication connection between a network element of the system and at least one other network element is realized through at least one communication interface 53 (which may be wired or wireless), wherein Internet, a wide area network, a local network, and a metropolitan area network may be used.

The bus 52 may be an ISA bus, a PCI bus, or an EISA bus, or the like. The bus may be divided into an address bus, a data bus, a control bus, etc. For convenience of illustration, the bus is represented by one double-headed arrow only in FIG. 4, but it does not mean that there is only one bus or one type of bus.

The memory 51 is used to store a program, and after the processor 50 receives an execution instruction, the method executed by the device defined by the flow process disclosed in any of the embodiments of the present disclosure may be applied to the processor 50 or implemented by the processor 50.

The processor 50 may be an integrated circuit chip with a signal processing capacity. In an implementation process, the steps in the foregoing methods may be completed using an integrated logic circuit of hardware in the processor 50 or an instruction in a form of software. The above-mentioned processor 50 may be a general-purpose processor, including a Central Processing Unit (CPU), a Network Processor (NP); and may also be a Digital Signal Processor (DSP), an Application Specific Integrated Circuit (ASIC), a Field-Programmable Gate Array (FPGA) or other programmable logic device, a discrete gate, or a transistor logic device, and a discrete hardware assembly. The methods, steps, and logic diagrams disclosed in the embodiment of the present disclosure may be implemented or executed by the processor. The general purpose processor may be a microprocessor or the processor may be any conventional processor, or the like. Steps of the methods disclosed with reference to the embodiments of the present disclosure may be directly executed and accomplished by means of a hardware decoding processor or may be executed and accomplished using a combination of hardware and software modules in the decoding processor. The software module may be located in a mature storage medium in the art, such as a random access memory, a programmable read-only memory, or an electrically erasable programmable memory, a register, etc. The storage medium is located in the memory 51. The processor 50 reads information from the memory 51 and completes the steps of the foregoing methods in combination with the hardware of the processor.

Fourth Embodiment

The embodiments of the present disclosure also provide a computer-readable storage medium, wherein a computer program is stored in the computer-readable storage medium, and the computer program, when executed by a processor, implements the steps of the method according to the first embodiment.

In the description of the embodiments of the present disclosure, unless otherwise clearly defined, terms such as "installation", "connected" and "connection", etc., should be understood broadly, for example, the connection may be fixed connection, is detachable connection or integral connection; may be mechanical connection, and may also be electrical connection; may be direct connection, may also be indirect connection through an intermediate medium, and may also be internal communication of two elements. The specific meaning of the above terms in the present disclosure can be understood in a specific case by those of ordinary skills in the art.

In the description of the present disclosure, it should be noted that the orientations or positional relationships indicated by the terms such as "center", "upper", "lower", "left", "right", "vertical", "horizontal", "inner", "outer" and the like, refer to the orientations or positional relationships shown in the drawings, which are only intended to facilitate describing the disclosure and simplifying the description, and do not indicate or imply that the indicated devices or elements must have a specific orientation, be constructed and operated in a specific orientation, and therefore cannot be understood as a limitation of the present disclosure. Moreover, the terms "first", "second" and "third" are used for descriptive purposes only and cannot be understood as indicating or implying relative importance.

In the several embodiments provided in the present application, it should be understood that the disclosed systems, devices and methods may be implemented in other ways. The device embodiments described above are merely illustrative. For example, the division of the units is only one logical function division. In practice, there may be other division methods. For another example, multiple units or components may be combined or integrated into another system, or some characteristics may be ignored or not performed. In addition, the illustrated or discussed mutual coupling or direct coupling or communication connection may be indirect coupling or communication connection through some communication interfaces, devices or units, and may be in electrical, mechanical or other forms.

The units illustrated as separation parts may either be or not physically separated, and the parts displayed as units may either be or not physical units, i.e., the parts displayed as units may be located in one place or distributed to multiple network units. Some or all of the units may be selected according to actual needs to achieve the objectives of the solutions in the embodiments.

In addition, each functional unit in each embodiment of the present disclosure may be integrated in one processing unit, or each unit may exist alone physically, or two or more units may be integrated in one unit.

Finally, it should be noted that the above embodiments are only specific embodiments of the present disclosure, which are used to illustrate the technical solutions of the present disclosure, but are not intended to limit the technical solutions. The protection scope of the present disclosure is not limited to this. Although the present disclosure has been described in detail with reference to the aforementioned embodiments, it should be understood by those of ordinary skills in the art that anyone familiar with the technical field can still modify or easily think of changes to the technical solutions described in the aforementioned embodiments within the technical scope disclosed by the present disclosure, or replace some of the technical characteristics equally; however, these modifications, changes or replacements do not make the essence of the corresponding technical solutions deviate from the spirit and scope of the technical solutions of the embodiments of the present disclosure, and should be covered within the protection scope of the present disclosure. Therefore, the protection scope of the present disclosure should be subjected to the protection scope of the claims.

What is claimed is:

1. A method for determining a quality grade of video data, comprising:
  acquiring, by at least one processor, a plurality of initial electroencephalogram (EEG) data, wherein the initial EEG data comprises electroencephalogram emotion data generated by a target object watching videos with degraded quality and emotional response electroencephalogram data generated by the target object watching a plurality of pictures and videos;
  determining, by the at least one processor, an initial EEG data set based on the plurality of initial EEG data, wherein the initial EEG data set comprises a first sub-data set and a second sub-data set, the first sub-data set comprises a data set built on a basis of the emotional response electroencephalogram data, and the second sub-data set comprises a data set built on a basis of the electroencephalogram emotion data;
  processing, by the at least one processor, the first sub-data set and the second sub-data set by using a characteristic-based transfer learning algorithm to obtain a third sub-data set and a fourth sub-data set, respectively, wherein the characteristic-based transfer learning algorithm includes characteristic mapping by assuming in Transfer Component Analysis (TCA); and
  determining, by the at least one processor, a quality evaluation grade of the video data with the degraded quality by building a support vector machine model based on the third sub-data set and inputting the fourth sub-data set into the support vector machine model to obtain the quality evaluation grade of the video data with the degraded quality.

2. The method according to claim 1, wherein determining the initial EEG data set based on the plurality of initial EEG data comprises:

preprocessing the plurality of initial EEG data to obtain a plurality of target EEG data;
performing characteristic extraction on the plurality of target EEG data to obtain a plurality of wavelet packet coefficient characteristics; and
building the first sub-data set by using a wavelet packet coefficient characteristic of the electroencephalogram emotion data, and building the second sub-data set by using a wavelet packet coefficient characteristic of the emotional response electroencephalogram data.

3. The method according to claim 2, wherein preprocessing the plurality of initial EEG data to obtain the plurality of target EEG data comprises:
determining a reference potential of the initial EEG data;
calibrating the initial EEG data based on the reference potential to obtain intermediate EEG data; and
filtering and clipping the intermediate EEG data to obtain the plurality of target EEG data.

4. The method according to claim 3, wherein the initial EEG data comprises a plurality of scalp electrode signals; and
determining the reference potential of the initial EEG data comprises:
determining location information of an electrode corresponding to each scalp electrode signal on a scalp of the target object;
determine a target location by using the location information, and determining the reference potential according to a potential of an electrode corresponding to the target location, wherein the target location refers to bilateral ears of the target object; or
calculating a mean potential of potentials corresponding to the plurality of scalp electrode signals; and
determining the mean potential as the reference potential.

5. The method according to claim 3, wherein filtering and clipping the intermediate EEG data to obtain the plurality of target EEG data comprises:
filtering the intermediate EEG data to obtain filtered intermediate EEG data;
performing independent principal components analysis on the filtered intermediate EEG data to determine a target signal in the filtered intermediate EEG data, wherein the target signal is a signal with a maximum energy value in the filtered intermediate EEG data; and
deleting the target signal to obtain the plurality of target EEG data.

6. The method according to claim 2, wherein performing characteristic extraction on the plurality of target EEG data to obtain the plurality of wavelet packet coefficient characteristics comprises:
performing wavelet packet decomposition on the plurality of target EEG data to obtain a sub-band tree, wherein each sub-band contains one or more nodes;
determining a wavelet packet coefficient of each sub-band; and
extracting a wavelet packet coefficient characteristic based on the wavelet packet coefficient of each sub-band, wherein the wavelet packet coefficient characteristic comprises: wavelet energy of each node, wavelet entropy of each node, an energy recursion efficiency of a target waveband, and an absolute power.

7. An electronic device, comprising a memory and at least one processor, wherein the memory is configured for storing a program supporting the processor to execute the method according to claim 1, and the at least one processor is configured for executing the program stored in the memory.

8. A non-transitory computer-readable storage medium, wherein a computer program is stored in the non-transitory computer-readable storage medium, and the computer program, when executed by at least one processor, implements the method according to claim 1.

9. An apparatus for determining a quality grade of video data, wherein the apparatus includes at least one processor and a memory storing an instruction, and when the instruction is executed by the at least one processor, cause the apparatus for performing operations comprising:
acquiring a plurality of initial electroencephalogram (EEG) data, wherein the initial EEG data comprises electroencephalogram emotion data generated by a target object watching videos with degraded quality and emotional response electroencephalogram data generated by the target object watching a plurality of pictures and videos;
determining an initial EEG data set based on the plurality of initial EEG data, wherein the initial EEG data set comprises a first sub-data set and a second sub-data set, the first sub-data set is a data set built on a basis of the emotional response electroencephalogram data, and the second sub-data set is a data set built on a basis of the electroencephalogram emotion data;
processing the first sub-data set and the second sub-data set by using a characteristic-based transfer learning algorithm to obtain a third sub-data set and a fourth sub-data set, respectively, wherein the characteristic-based transfer learning algorithm includes characteristic mapping by assuming in Transfer Component Analysis (TCA); and
determining a quality evaluation grade of the video data with the degraded quality by building a support vector machine model based on the third sub-data set and inputting the fourth sub-data set into the support vector machine model to obtain the quality evaluation grade of the video data with the degraded quality.

* * * * *